United States Patent [19]

Thompson et al.

[11] Patent Number: 5,093,493
[45] Date of Patent: Mar. 3, 1992

[54] 4-AMINO-BENZO[B]THIENO[2,3-B] PYRIDINES USEFUL IN THE TREATMENT OF CNS DISORDERS

[75] Inventors: Mervyn Thompson; Ian T. Forbes; Christopher N. Johnson, all of Harlow, England

[73] Assignee: Beecham Group p.l.c., Brentford, England

[21] Appl. No.: 494,792

[22] Filed: Mar. 12, 1990

Related U.S. Application Data

[63] Continuation of Ser. No. 300,824, Jan. 23, 1989, abandoned.

[30] Foreign Application Priority Data

Jan. 22, 1988 [GB] United Kingdom ............... 8801491

[51] Int. Cl.$^5$ ............... C07D 413/14; C07D 409/02; C07D 513/04; C07D 513/14
[52] U.S. Cl. ................................. 544/126; 544/361; 546/80
[58] Field of Search ............... 544/126, 361; 546/80; 540/481, 544, 575, 597; 514/232.8, 254, 291

[56] References Cited

U.S. PATENT DOCUMENTS 4,703,051 10/1987 Adachi et al. .................... 546/80

FOREIGN PATENT DOCUMENTS 0126970 12/1984 European Pat. Off. .
0249301 12/1987 European Pat. Off. .
2435025 2/1975 Fed. Rep. of Germany .

OTHER PUBLICATIONS

Lalezari, "Synthesis of 4-Aminothieno(2,3-b)-pyridine-5-carboxylic Acids (1)", J. Heterocycl. Chem., vol. 16, 1979, p. 603.
Gewald et al., "Synthesis of 4-Amino—Thiono[2,3-b]-pyridine", Monatshefte für Chemie 110, 1189–1196 (1979).
CA 90:203910c, Ralezari, J. Heterocyclic Chem., 1979, 16(3), pp. 603–604.

Primary Examiner—Catherine S. Kilby Scalzo
Attorney, Agent, or Firm—Hopgood, Calimafde, Kalil, Blaustein & Judlowe

[57] ABSTRACT

Compounds of formula (I) or pharmaceutically acceptable salts thereof:

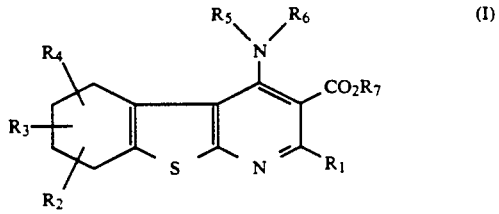

wherein:

$R_1$ is hyudrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$, $R_3$ and $R_4$ are independently selected from hydrogen, $C_{1-6}$ alkyl, $C_{1-6}$ alkoxycarbonyl, $C_{1-6}$ alkylthio, $C_{2-7}$ alkanoyl, trifluoromethyl, cyano, carbamoyl and carboxy, and phenyl or phenyl $C_{1-4}$ alkyl in which any phenyl moiety is optionally substituted by $C_{1-6}$ alkyl, $C_{1-6}$ alkoxy, $C_{1-6}$ alkoxy carbonyl, $C_{1-6}$ alkylthio, hydroxy, $C_{2-7}$ alkanoyl, chloro, fluoro, trifluoromethyl, nitro or amino optionally substituted by one or two $C_{1-6}$ alkyl groups or by $C_{2-7}$ alkanoyl, cyano, carbamoyl and carboxy;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_{2-6}$ polymethylene optionally interrupted by oxygen or $NR_8$ wherein $R_8$ is hydrogen or $C_{1-6}$ alkyl optionally substituted by hydroxy; and $-CO_2R_7$ is a pharmaceutically acceptable ester group, are provided for use in the treatment or prophylaxis of CNS disorders, in particular anxiety or depression.

7 Claims, No Drawings

4-AMINO-BENZO[B]THIENO[2,3-B] PYRIDINES USEFUL IN THE TREATMENT OF CNS DISORDERS

This is a continuation of Ser. No. 300,824, filed Jan. 23, 1989, now abandoned.

This invention relates to compounds having pharmacological activity, to a process for their preparation, to compositions containing them and to their use in the treatment of mammals.

EP-A-0 249 301 (Beecham Group plc) discloses a class of compounds having anxiolytic and/or antidepressant activity which compounds are 4-amino-9H-pyrido[2,3-b]-indole-3-carboxylate derivatives.

I. Lalezari, Journal of Heterocyclic Chemistry, 16, 603, (1979) describes the preparation of 4-amino-thieno[2,3-b]pyridine-5-carboxylate derivatives of formula (A):

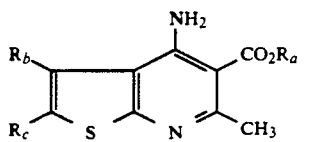

(A)

wherein $R_a$ is hydrogen or ethyl; $R_b$ and $R_c$ are methyl, or $R_b$ and $R_c$ together are —$(CH_2)_n$—where n is 3, 4 or 5.

No pharmacological activity is attributed to compounds of formula (A).

A class of compounds has now been discovered, which compounds have been found to have CNS activity, in particular anxiolytic and/or anti-depressant activity.

Accordingly, the present invention provides a compound of formula (I) or a pharmaceutically acceptable salt thereof:

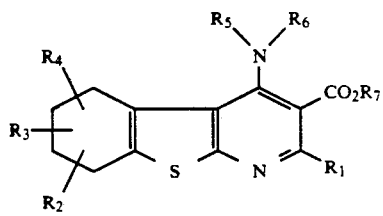

(I)

wherein:

$R_1$ is hydrogen $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$, $R_3$ and $R_4$ are independently selected from hydrogen, $C_{1-6}$ alkyl, $C_{1-6}$ alkoxycarbonyl, $C_{1-6}$ alkylthio, $C_{2-7}$ alkanoyl, trifluoromethyl, cyano, carbamoyl and carboxy, and phenyl or phenyl $C_{1-4}$ alkyl in which any phenyl moiety is optionally substituted by $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro or amino optionally substituted by one or two $C_{1-6}$ alkyl groups or by $C_{2-7}$ alkanoyl, cyano, carbamoyl and carboxy;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-$(C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_{2-6}$ polymethylene optionally interrupted by oxygen or $NR_8$ wherein $R_8$ is hydrogen or $C_{1-6}$ alkyl optionally substituted by hydroxy; and —$CO_2R_7$ is a pharmaceutically acceptable ester group, for pharmaceutical use.

By pharmaceutical use is meant the treatment or prophylaxis of disorders in mammals including humans. Compounds of formula (I) and their pharmaceutically acceptable salts have anxiolytic and/or antidepressant activity and are of particular use in the treatment or prophylaxis of CNS disorders, in particular anxiety or depression. Thus the invention also provides a compound of formula (I) or a pharmaceutically acceptable salt thereof, for use in the treatment or prophylaxis of CNS disorders, in particular anxiety or depression.

The invention further provides a method of treatment or prophylaxis of CNS disorders, in particular anxiety or depression in mammals including humans, which comprises administering to the sufferer an anti-depressant or anxiolytic effective amount of a compound of formula (I) or a pharmaceutically acceptable salt thereof.

In another aspect, the invention provides the use of a compound of formula (I) or a pharmaceutically acceptable salt thereof in the preparation of a medicament for the treatment or prophylaxis of CNS disorders, in particular anxiety or depression.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of CNS disorders, such as anxiety or depression will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.01 to 100 mg/kg; and such therapy may extend for a number of weeks or months.

Within the above indicated dosage range, no adverse toxicological effects are indicated with the compounds of the invention.

Alkyl moieties within the variables $R_1$ to $R_6$ are preferably $C_{1-3}$ alkyl, such as methyl, ethyl and n- and iso-propyl.

Values for $R_1$ include hydrogen, methyl, ethyl, n- and iso-propyl, phenyl and benzyl. Preferably, $R_1$ is methyl.

Values for $R_2$, $R_3$ and $R_4$ include hydrogen or $C_{1-4}$ alkyl. Preferably, two of $R_2$, $R_3$ and $R_4$ represent hydrogen, and more preferably $R_2$, $R_3$ and $R_4$ each represent hydrogen.

Values for $R^5$ and $R^6$ include hydrogen, methyl, ethyl, n- and iso-propyl, n-, sec-, iso- and tert-butyl, n-, sec, iso- and neo-pentyl,cyclopentyl, cyclohexyl, cycloheptyl, cyclopentyl-$C_{1-4}$ alkyl, cyclohexyl-$C_{1-4}$ alkyl and cycloheptyl-$C_{1-4}$ alkyl, where values for $C_{1-4}$ alkyl include methylene and ethylene, but-2-enyl, but-3-enyl,-methylprop-2-enyl, formyl, acetyl, propionyl, methylsulphonyl, 3-dimethylaminobutyl, 3-oxobutyl, 3-hydroxybutyl, phenyl, benzyl, benzoyl, benzylcarbonyl and benzenesulphonyl, or $R_5$ and $R_6$ together form $C_4$ or $C_5$ polymethylene, —$(CH_2)_2$—O—$(CH_2)_2$—or —$(CH_2)_2$—$NR_8$—$(CH_2)_2$—where $R_8$ is preferably methyl.

Preferably $R_5$ is hydrogen and $R_6$ is hydrogen or $C_{1-6}$ alkyl, for example methyl.

There is a favoured group of compounds within formula (I) of formula (II) or a pharmaceutically acceptable salt thereof:

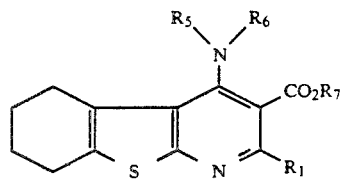

(II)

wherein $R_1$, $R_5$, $R_6$ and $R_7$ are as defined in formula (I).

Preferred values for $R_1$, $R_5$ and $R_6$ are as described under formula (I).

There is a preferred group of compounds within formula (II) of formula (III) or a pharmaceutically acceptable salt thereof:

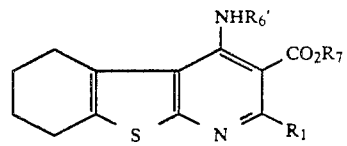

(III)

wherein $R_6$ is hydrogen or $C_{1-6}$ alkyl and $R_1$ and $R_7$ are as defined in formula (I).

Preferred values for $R_1$ and $R_6'$ are as described for the corresponding variables in formula (I).

The invention further provides novel compounds within formula (I), wherein the variable groups are as defined in formula (I) with the proviso that when $R_1$ is methyl and $R_2$, $R_3$, $R_4$, $R_5$ and $R_6$ are hydrogen, $R_7$ is other than ethyl. Such compounds are hereinafter referred to as compounds of formula (Ia).

The compounds of the formula (I) can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulphonic.

Suitable examples of pharmaceutical esters of the compounds of formula (I) include $C_{1-6}$ alkyl esters, such as methyl, ethyl, n- and iso-propyl, n-, sec- and tert-butyl esters, $C_{2-6}$ alkenyl esters such as vinyl, prop-1-enyl, prop-2-enyl, 1-methylvinyl, but-1-enyl, but-3-enyl, 1-methylenepropyl and 1-methylprop-2-enyl, (in both their E and Z forms where stereoisomerism exists), $C_{2-6}$ alkynyl esters such as prop-2-ynyl, $C_{3-6}$ cycloalkyl esters and $C_{3-6}$ cycloalkyl-$C_{1-4}$ alkyl esters such as cyclopropylmethyl. Preferably the pharmaceutically acceptable ester is the methyl, ethyl, propyl, prop-2-enyl or prop-2-ynyl ester, i.e. $R_7$ is methyl, ethyl, propyl, prop-2-enyl or prop-2-ynyl.

It will be appreciated that the compounds of formula (I) in which $R_5$ or $R_6$ is hydrogen may exist tautomerically in more than one form. The invention extends to each of these forms and to mixtures thereof.

Compounds of formula (I) may also form solvates such as hydrates, and the invention also extends to these forms. When referred to herein, it is understood that the term "compound of formula (I)" also includes solvates thereof.

A process for the preparation of a compound of formula (I), or a pharmaceutically acceptable salt thereof comprises the reaction of a compound of formula (IV):

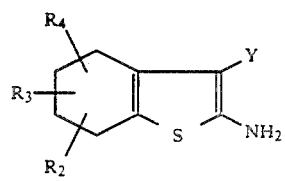

(IV)

with a compound of formula (V):

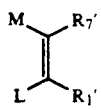
(V)

wherein $R_1'$ is $R_1$ as defined in formula (I) or a group convertible thereto, $R_2$, $R_3$ and $R_4$ are as defined in formula (I), $R_7'$ is $-CO_2R_7$ as defined in formula (I) or an electron-withdrawing group convertible to $-CO_2R_7$, L is a leaving group and M is hydrogen or L and M together represent a bond, and Y is a group CN or $COL_1$, where $L_1$ is a leaving group; and thereafter, optionally or as necessary, when Y is a group $COL_1$, converting the resulting hydroxy group to a leaving group and reacting the latter with a compound $HNR_5R_6$, converting $R_1'$ when other than $R_1$ to $R_1$, converting $R_7'$ when other than $-CO_2R_7$ to $-CO_2R_7$, interconverting $R_5$ or $R_6$, and/or forming a pharmaceutically acceptable salt of the compound of formula (I).

Suitable examples of the leaving group L include halogens, such as chloro and bromo, hydroxy, $C_{1-6}$ acyloxy such as acetoxy or $C_{1-6}$ alkoxy, such as methoxy or ethoxy, preferably methoxy. When L is hydroxy, it will be appreciated that the compound of formula (V) exists in more than one tautomeric form.

The reaction of compounds of formulae (IV) and (V) comprises a condensation step followed by a cyclisation step, the acyclic enamine intermediate optionally being isolated before cyclisation.

The condensation step may be carried out under conditions conventional for condensation reactions, at elevated temperatures in an inert solvent such as toluene, benzene, ethanol, pyridine, dimethylformamide or dioxan, optionally in the presence of a catalyst such as para-toluene-sulphonic acid, with water separation.

The cyclisation of the enamine may also be carried out under conventional conditions, in the presence of a strong base such as an alkali metal alkoxide, for example sodium methoxide in a suitable solvent such as methanol, at elevated temperature, or in the presence of a Lewis acid such as $ZnCl_2$, $SnCl_4$ or $CuOCOCH_3$ in n-butyl acetate at elevated temperature.

Suitable examples of groups $R_7'$ include the groups hereinbefore described for $-CO_2R_7$, $CO_2Q$ where Q is a protecting group such as benzyl wherein the benzyl moiety is optionally substituted in the phenyl ring by one or two of halogen, $CF_3$, $C_{1-6}$ alkoxy, $C_{1-6}$ alkyl or nitro, or cyano and $-CONR_9R_{10}$ where $R_9$ and $R_{10}$ are independently selected from hydrogen, $C_{1-6}$ alkyl and phenyl or phenyl $C_{1-4}$ alkyl optionally substituted as described above for optional substituents in the phenyl ring of a benzyl ester, or together form a $C_{2-6}$ polymethylene chain optionally interrupted by oxygen or $NR_{11}$ wherein $R_{11}$ is hydrogen or $C_{1-6}$ alkyl, e.g. morpholino or piperazino.

A protecting group Q may be removed by conventional hydrolysis or hydrogenolysis to yield the free acid which can then be esterified under conventional conditions by reaction with the appropriate alcohol $R_7OH$, optionally with prior conversion of the acid to the acid chloride by reaction with a suitable chlorinating agent such as thionyl chloride, or with an alkylating agent $R_7X$ where X is a leaving group such as chloro, bromo or iodo, in the presence of a suitable base such as potassium carbonate.

An intermediate amide may be hydrolysed to the free acid which can then be esterified as described above.

An $R_7'$ cyano group may be converted under anhydrous conditions to an imino ester by reaction with the appropriate alcohol $R_7OH$ and then hydrolysed to the group $-CO_2R_7$.

Suitable examples of a leaving group $L_1$ when Y is $COL_1$, include hydroxy and, more preferably, alkoxy such as ethoxy or methoxy. The reaction of the compounds of formulae (IV) and (V) gives a resulting compound having an hydroxy group in the 4-position of the pyridine ring. The hydroxy group may be converted to a leaving group such as those defined above for L, preferably halo such as chloro, by reaction with a halogenating agent such as phosphorus oxychloride or phosphorus oxybromide. The leaving group may be displaced by the compound $HNR_5R_6$ under conventional conditions for nucleophilic aromatic displacements, at elevated temperatures in an inert solvent such as toluene, methanol, ethanol, pyridine, dimethylformamide or dioxan. Alternatively, the reaction may be carried out in neat $HNR_5R_6$ which functions as the solvent.

Conversion of $R_5$ and $R_6$ hydrogen to other $R_5/R_6$ may be carried out in accordance with conventional procedures for the alkylation or acylation of a primary amine. Acylation may be carried out by reaction with the appropriate acyl halide. However, $R_5/R_6$ other than hydrogen or acyl groups are preferably introduced via the route in which Y is $COL_1$ in the compound of formula (IV), by displacement of the leaving group with the compound $HNR_5R_6$ as discussed above.

For the preparation of compounds of formula (I) in which $R_1$ is hydrogen, the compound of formula (V) may be used in which L and M together represent a bond or L is hydroxy and M is hydrogen, and $R_1'$ is a $C_{1-6}$ alkoxycarbonyl group. The reaction with the compound of formula (IV) may then be followed by a decarboxylation step to give $R_1$ hydrogen. Alternatively, a compound of formula (V) may be used in which L is a leaving group and $R_1'$ is hydroxy. In the resulting compound, the $R_1'$ hydroxy may be converted to hydrogen by first replacing it by chloro by conventional chlorination with a chlorinating agent such as phosphorus oxychloride followed by reductive dehalogenation under conventional conditions, for example zinc in acetic acid.

Pharmaceutically acceptable salts may be prepared conventionally by reaction with the appropriate acid or derivative.

It will be appreciated that the present invention also provides a process for the preparation of the novel compounds of formula (Ia).

A class of intermediates comprises compounds of formula (VI) or a salt thereof:

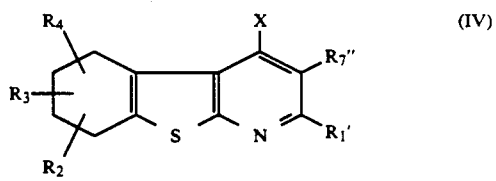
(IV)

wherein $R_1'$ is as defined in formula (V), $R_7''$ is $R_7'$ as defined in formula (V), X is $NH_2$, OH or chloro and $R_2$, $R_3$ and $R_4$ are as defined in formula (IV), provided that when X is $NH_2$ and $R_1'$ is $R_1$, $R_7''$ is other than $-CO_2R_7$, when X is $NH_2$, $R_1'$ is methyl and $R_2$, $R_3$, and $R_4$ are hydrogen, $R_7'$ is other than $CO_2H$, when X is $NH_2$ and $R_1'$, $R_2$, $R_3$ and $R_4$ are hydrogen, $R_7''$ is other than cyano, and when X is OH and $R_1'$, $R_2$, $R_3$ and $R_4$ are hydrogen, $R_7''$ is other than $CO_2H$ or $CO_2C_2H_5$.

The compound of formula (VI) in which $R_7''$ is $CO_2H$, X is $NH_2$, $R_1'$ is methyl and $R_2$, $R_3$ and $R_4$ are hydrogen has been described by I. Lalezari, J. Het. Chem., 16, 03, (1979).

The compounds of formula (VI) in which $R_7''$ is $CO_2H$ and $CO_2C_2H_5$, X is OH and $R_1'$, $R_2$, $R_3$ and $R_4$ are hydrogen have been described in Belgian Patent 817950 (Takeda).

The compound of formula (VI) in which $R_7''$ is cyano, X is $NH_2$ and $R_1'$, $R_2$, $R_3$ and $R_4$ are hydrogeh has been described by K. Gewald et al., Monatsh Chem., 1070, 110(5), 1189.

Novel compounds of formula (VI) also form part of the invention.

Compounds of formulae (IV) and (V) are known or can be prepared by analogous processes to those used for preparing known compounds. In particular, compounds of formula (IV) may be prepared using procedures similar to that in K. Gewald et al.; Chem. Ber. 1966, 94. The compound of formula (IV) in which $R_2$, $R_3$ and $R_4$ are hydrogen and Y is ethoxycarbonyl is commercially available. The compound of formula (V) in which $R_1'$ is phenyl, M is hydrogen, L is ethoxy and $R_7'$ is ethoxycarbonyl is described by V.L. Leighton, American Chem. Journal, 1898, 20, 133.

The following Examples illustrate the preparation of pharmacologically active compounds of the invention. Examples 1 to 5, 7 and 8 illustrate the preparation of novel compounds of formula (Ia). The following Descriptions illustrate the preparation of intermediates to the compounds of the present invention.

DESCRIPTION 1

2-Amino-3-cyano-4,5,6 7-tetrahydrobenzo[b]thiophene (D1)

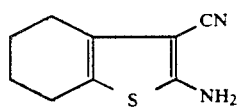

The title compound was prepared using a procedure similar to that in K. Gewald et al.; Chem. Ber. 1966, 94 (67% yield; m.p. 146–7° C.).

DESCRIPTION 2

4-Hydroxy-2-methyl-5,6,7,8-tetrahydrobenzo[b]-thieno[2,3]pyridine-3-carboxylic acid, ethyl ester (D2)

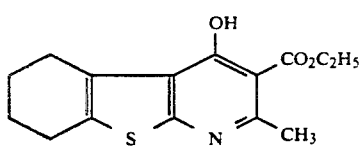

Ethyl 2-amino-4,5,6,7-tetrahydrobenzo[b]thiophene-3carboxylate (5.0g; 22mM) and ethyl 3-ethoxycrotonate (4.17g; 26.4mM) were converted into the title compound (5.8g; 90%).
m.p. 135–6°.
Found: C, 61.58; H, 5.86; N, 4.72.
$C_{15}H_{17}NO_3S$ requires C, 61.83; H, 5.88; N, 4.8%.

DESCRIPTION 3

4-Chloro-2-methyl-5,6,7,8-tetrahydrobenzo[b]thieno-[2,3-b]pyridine-3-carboxylic acid, ethyl ester (D3)

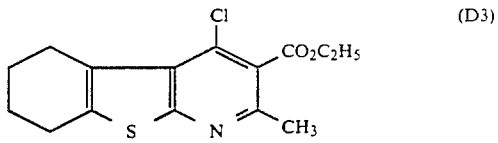

A solution of D2 (10g; 34.4mM) in phosphorus oxychloride (100ml) was heated under reflux for 4h and then evaporated to dryness. The residue was partitioned between aqueous sodium bicarbonate and dichloromethane and the organic phase dried ($Na_2SO_4$). Evaporation in vacuo followed by flash chromatography on silica gave the title compound (6.75g; 63%).

EXAMPLE 1

4-Amino-2-methyl-5,6,7,8-tetrahydrobenzo[b]thieno-[2,3-b]pyridine-3-carboxylic acid, methyl ester, (E1)

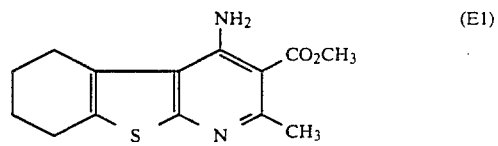

A solution of the amino nitrile D1 (7.27g; 41mM) and methyl β-methoxycrotonate (5.34g; 41mM) in toluene (150ml) was heated at reflux for 96h. The reaction mixture was cooled, filtered and treated with a 1M solution of sodium methoxide in methanol (42ml). The resulting dark solution was refluxed under nitrogen for 5h. The reaction mixture was cooled and shaken with brine (150ml). The organic phase was separated, then dried over anhydrous sodium sulphate and evaporated in vacuo to give the title compound E1 as an off-white solid (8.75g; 78%).
m.p. 185–93° (from methanol)
NMR ($CDCl_3$) δ: 1.82 (4H, m), 2.64 (3H, s), 2.85 (4H, m), 3.85 (3H, s), 6.46 (2H, s, ex $D_2O$).
Found: C, 60,60; H, 5.69; N, 10.02.
$C_{14}H_{16}N_2O_2S$ requires C, 60.85; H, 5.84; N 10.14%.
Found M+276.0938.
$C_{14}H_{16}N_2O_2S$ requires 276.0932.

Example 2

4-Amino-2-methyl-5,6,7,8-tetrahydrobenzo[b]-thieno[2,3-b]pyridine-3-carboxylic acid, 2-propenyl ester (E2)

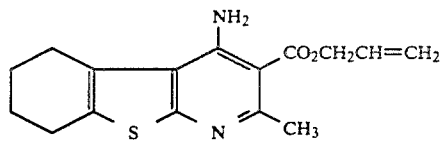

The title compound E2 was prepared from the methyl ester E1 by hydrolysis using aqueous ethanolic sodium hydroxide at reflux followed by alkylation with allyl bromide using potassium carbonate in dimethylformamide.
m.p. 125–6° (from methanol)
Found: C, 63.33; H, 6.09; N, 9.16.

C$_{16}$H$_{18}$N$_2$O$_2$S requires C, 63.55; N, 6.00; N, 9.26%.

EXAMPLE 3

4-Amino-2-methyl-5,6,7,8-tetrahydrobenzo[b]-thieno[2,3-b]pyridine-3-carboxylic acid, 2-propynl ester (E3)

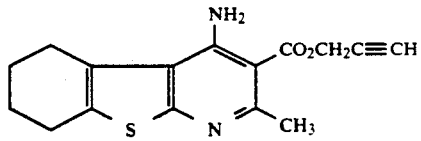

The title compound E3 was prepared from the methyl ester E1 and 2-propynyl bromide using a method similar to that of Example 2.
m.p. 158-60° (from methanol).
Found: C, 64.10; H, 5.29; N, 9.23.
C$_{16}$H$_{16}$N$_2$O$_2$S requires C, 63.98; H, 5.37; N, 9.33%.

EXAMPLE 4

4-Amino-2-phenyl-5,6,7,8-tetrahydrobenzo[b]thieno-[2,3-b]pyridine-3-carboxylic acid, ethyl ester (E4)

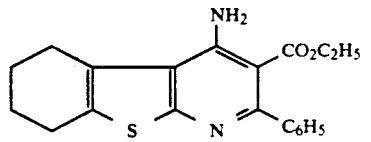

The title compound was prepared in 20% overall yield from D1 and ethyl β-ethoxycinnamate using a method similar to that of Example 1.
m.p. 54-6° (from ethanol).
Found: C, 67.63; H, 5.87; N, 7.80.
C$_{20}$H$_{20}$N$_2$O$_2$S requires C, 68.16; H, 5.72; N, 7.95%.

EXAMPLE 5

4-Amino-2-methyl-5,6,7,8-tetrahydrobenzo[b]thieno-[2,3-b]pyridine-3-carboxylic acid, isopropyl ester (E5)

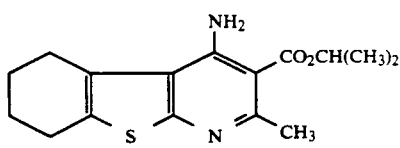

The title compound was prepared from the ethyl ester (E6) and 2-iodopropane using a method similar to that of Example 2.
m.p. 113-115° C. (from ether).
Found: C, 63.10; H, 6.48; N, 9.23.
C$_{16}$H$_{20}$N$_2$O$_2$S requires C, 63.13; H, 6.62; N, 9.20%.

EXAMPLE 6

4-Amino-2-methyl-5,6,7,8-tetrahydrogenzo[b]thieno-[2,3,-b]pyridine-3-carboxylic acid, ethyl ester (E6)

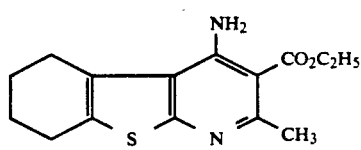

The title compound was prepared in 22% overall yield from D1 and ethyl 3-ethoxycrotonate using a method similar to that described in Example 1.
m.p. 133-136° C. (from ethanol).
Found: C, 62.48; H, 6.34; N, 9.61.
C$_{15}$H$_{18}$N$_2$O$_2$S requires C, 62.04; H, 6.25; N, 9.65%.

EXAMPLE 7

2-Methyl-4-methylamino-5,6,7,8-tetrahydrobenzo[b]-thieno[2,3-b]pyridine-3-carboxylic acid, ethyl ester (E7)

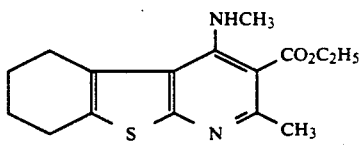

The title compound was prepared in 20% yield from D3 and methylamine using an autoclave followed by chromatography on Kieselgel 60 in dichloromethane.
m.p. 110-112° (from ethyl acetate-petrol).
Found: C, 62.85; H, 6.58; N, 9.21.
C$_{16}$H$_{20}$N$_2$O$_2$S requires C, 63.13; H, 6.62; N, 9.20%.
NMR (CDCl$_3$) δ:
1.43 (3H, t, J=7Hz), 1.80-1.97 (4H, m), 2.50 (3H, s), 2.75-2.85 (2H, m), 2.93 (3H, d, J=5Hz), 2.96-3.03 (2H, m), 4.40 (2H, q, J=7Hz), 5.07-5.28 (1H, br).

EXAMPLE 8

2-Methyl-4-methylamino-5,6,7,8-tetrahydrobenzo[b]-thieno[2,3-b]pyridine-3-carboxylic acid, 2propynyl ester (E8)

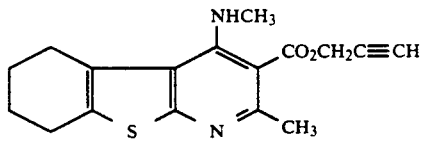

The title compound was prepared from D3 and methylamine in an autoclave followed by hydrolysis and esterification with propargyl bromide using a method similar to that of Example 2.
m.p. 108-9° C.

Pharmacological Data

Geller-Seifter Procedure

Potential anxiolytic properties have been evaluated using the Geller-Seifter procedure based on that originally described by Geller and Seifter, (1960) Psychopharmacologia, 1, 482-492. This procedure has been shown to be selective for drugs with anxiolytic properties (Cook and Sepinwall, (1975) "Mechanism of Action of Benzodiazepines" ed. Costa, E. and Greengard, P., Raven Press, New York, pp. 1-28).

Rats are trained on a variable interval 30 sec schedule (VI30) to press a lever in order to obtain food reward. The 5 min sessions of the VI30 schedule alternate with 2-5 min of a schedule (FR5) in which every 5th lever press is followed by presentation of a food pellet paired with a 0.5 sec mild footshock. The total study lasts approximately 30 mins. Rats typically respond with high rates of lever pressing under the VI30 schedule and low response rates under the FR5 'conflict' session.

Anxiolytic drugs increase the suppressed response rates of rats in 'conflict' session.

Drugs are administered intraperitoneally or orally to groups of 3-8 rats 30 min before testing.

The results are expressed as the percentage increase in square root of the total number of lever presses in the FR5 'conflict' session. Square root transformation is necessary to normalise the data for statistical analysis using parametric methods (ANOVA).

Testing Results

The activity of the following compounds in the above test is detailed in the following Table.

| Compound | dose mg/kg | increase in responding in the 'conflict' session |
|---|---|---|
| Example 1 (E1) | 50 p.o. | +93% |
| Example 2 (E2) | 20 p.o. | +21% |
| Example 3 (E3) | 20 p.o. | +56% |
| Example 4 (E4) | 20 p.o. | +14% |

We claim:

1. A compound of formula (Ia) or a pharmaceutically acceptable salt thereof:

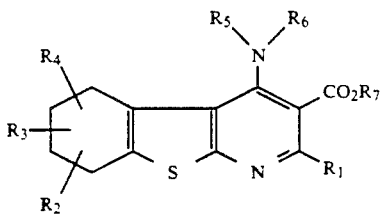

wherein $R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$, $R_3$ and $R_4$ are independently selected from hydrogen, $C_{1-6}$ alkyl, $C_{1-6}$ alkoxycarbonyl, $C_{1-6}$ alkylthio, $C_{2-7}$ alkanoyl, trifluoromethyl, cyano, carbamoyl and carboxy, and phenyl or phenyl $C_{1-4}$ alkyl n which any phenyl moiety is optionally substituted by $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro or amino optionally substituted by one or two $C_{1-6}$ alkyl groups or by $C_{2-7}$ alkanoyl, cyano, carbamoyl and carboxy;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl) amino $C_{1-6}$ alkyl, 3-oxobutyl, 3-hydroxybutyl, phenyl, phenyl $C_{1-4}$ alkyl, benzoyl, phenyl $C_{2-7}$ alkanoyl, or benzenesulphonyl, any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_4$ or $C_5$ polymethylene, —$(CH_2)_2$—O—$(CH_2)_2$—, or —$(CH_2)_2$—$NR_8$—$(CH_2)_2$—, wherein $R_8$ is hydrogen or $C_{1-6}$ alkyl optionally substituted by hydroxy, and —$CO_2R_7$ is a pharmaceutically acceptable ester group, with the proviso that when $R_1$ is methyl and $R_2$, $R_3$, $R_4$, $R_5$ and $R_6$ are hydrogen, $R_7$ is other than ethyl.

2. A compound according to claim 1 wherein $R_7$ is $C_{1-6}$ alkyl, $C_{2-6}$ alkenyl, $C_{2-6}$ alkynyl or $C_{3-6}$ cycloalkyl-$C_{1-4}$ alkyl.

3. A compound according to claim 1 wherein $R_1$ is hydrogen, $C_{1-3}$ alkyl, phenyl or benzyl.

4. A compound according to claim 1 wherein $R_2$, $R_3$ and $R_4$ are each hydrogen.

5. A compound according to claim 1 wherein $R_5$ and $R_6$ are independently hydrogen or $C_{1-6}$ alkyl.

6. A compound according to claim 1 wherein $R_1$ is methyl or phenyl, $R_2$, $R_3$ and $R_4$ are each hydrogen, $R_5$ and $R_6$ are independently hydrogen or methyl and $R_7$ is methyl, ethyl, propyl, prop-2-enyl or prop-2-ynyl.

7. A compound of formula (Ia) as in claim 1 selected from:

4-amino-2-methyl-5,6,7,8-tetrahydrobenzo[b]-thieno[2,3-b]pyridine-3-carboxylic acid, methyl ester;

4-amino-2-methyl-5,6,7,8-tetrahydrobenzo[b]-thieno[2,3-b]pyridine-3-carboxylic acid, 2-propenyl ester;

4-amino-2-methyl-5,6,7,8-tetrahydrobenzo[b]thieno-[2,3-b]pyridine-3-carboxylic acid, 2-propynyl ester;

4-amino-2-phenyl-5,6,7,8-tetrahydrobenzo[b]thieno-[2,3-b]pyridine-3-carboxylic acid, ethyl ester;

4-amino-2-methyl-5,6,7,8-tetrahydrobenzo[b]thieno-[2,3-b]pyridine-3-carboxylic acid, isopropyl ester;

2-methyl-4-methylamino-5,6,7,8-tetrahydrobenzo[b]-thieno-[2,3-b]pyridine-3-carboxylic acid, ethyl ester; and 2-methyl-4-methylamino-5,6,7,8-tetrahydrobenzo[b]-thieno-[2,3-b]pyridine-3-carboxylic acid, 2-propynl ester.

* * * * *